United States Patent [19]

Travers et al.

[11] Patent Number: 5,446,230
[45] Date of Patent: Aug. 29, 1995

[54] CHLORINATED, ALUMINA-BASED, BIMETALLIC CATALYST AND ITS USE IN THE ISOMERIZATION OF $C_4$-$C_6$ PARAFFINS

[75] Inventors: Christine Travers, Rueil Malmaison; Germain Martino, Poissy, both of France

[73] Assignee: Institut Francais Du Petrole, Rueil-Malmaison, France

[21] Appl. No.: 917,149

[22] PCT Filed: Dec. 10, 1991

[86] PCT No.: PCT/FR91/00992

§ 371 Date: Aug. 10, 1992

§ 102(e) Date: Aug. 10, 1992

[87] PCT Pub. No.: WO92/10289

PCT Pub. Date: Jun. 25, 1992

[30] Foreign Application Priority Data

Dec. 10, 1990 [FR] France .................. 90 15546

[51] Int. Cl.$^6$ .................. C07C 5/23; B01J 21/00; B01J 23/00
[52] U.S. Cl. .................. 585/748; 502/224; 502/227; 502/230; 502/231; 502/325; 502/349; 502/352; 502/355; 585/734; 585/737; 585/747
[58] Field of Search .................. 502/35, 308, 325, 355, 502/224, 227, 229, 230, 231, 349, 352; 585/734, 738, 747, 748

[56] References Cited

U.S. PATENT DOCUMENTS

| | | | |
|---|---|---|---|
| 3,723,554 | 3/1973 | Wilhelm | 585/482 |
| 3,919,340 | 11/1975 | Hayes | 585/668 |
| 4,009,220 | 2/1977 | Pollitzer et al. | 585/419 |
| 4,046,828 | 9/1977 | Pollitzer et al. | 585/419 |
| 4,804,803 | 2/1989 | Schmidt et al. | 585/748 |
| 4,964,975 | 10/1990 | Chao et al. | 208/139 |

FOREIGN PATENT DOCUMENTS 2137320 12/1972 France .
2545380 11/1984 France .
1276611 12/1957 Germany .

*Primary Examiner*—P. Achutamurthy
*Attorney, Agent, or Firm*—Millen, White, Zelano, & Branigan

[57] ABSTRACT

A catalyst is provided based on chlorinated eta alumina incorporating platinum and germanium and tin, as well as chlorine. This catalyst can be used in a process for the isomerization of a charge rich in normal $C_4$-$C_6$-paraffins, without hydrogen recycling.

23 Claims, No Drawings

CHLORINATED, ALUMINA-BASED, BIMETALLIC CATALYST AND ITS USE IN THE ISOMERIZATION OF $C_4$-$C_6$ PARAFFINS

The present invention relates to a novel bimetallic catalyst based on chlorinated alumina and its use in a process for the isomerization of normal $C_4$-$C_6$ paraffins not requiring hydrogen recycling.

BACKGROUND OF THE INVENTION

As a result of the elimination, mainly for ecological reasons, of lead alkyls in gasoline, the isomerization of normal paraffins having 4 to 6 carbon atoms is at present of considerable importance in the petroleum industry.

The isomerization of n-butane makes it possible to produce isobutane for the aliphatic alkylation of olefins and the synthesis of MTBE (methyl tert. butyl ether), respectively making it possible to produce an alkylate having a high octane number which can be incorporated into the gasoline pool and supply MTBE used as an octane additive.

The isomerization of normal $C_5$-$C_6$ paraffins makes it possible to transform these low octane number paraffins into high octane number isoparaffins.

Three different types of catalysts are conventionally used for carrying out this isomerization reaction:

Friedel-Crafts catalysts, such as aluminium chloride, which are used at low temperatures (approximately 20° to 130° C.);

catalysts based on metals of group VIII on halogenated alumina, which are used at medium temperatures (approximately 150° C.);

zeolitic catalysts incorporating a metal of group VIII deposited on a zeolite and which are used at high temperatures (250° C. and higher);

these catalysts leading to reduced octane number improvements, but have the advantage of being easier to obtain and are more resistant to poisons, but as a result of their low acidity, they cannot be used for n-butane isomerization.

Numerous patents deal with monometallic catalysts based on platinum deposited on a halogenated alumina, said catalysts being used in the isomerization of normal paraffins, in which the molar hydrogen/hydrocarbon ($H_2$/HC) ratios are relatively high, in order to prevent deactivation by coking linked with secondary reactions or the temporary presence of sulphur, cf. e.g. U.S. Pat. No. 2,906,798, in which $H_2$/HC is higher than 0.17, U.S. Pat. No. 2,993,398 and U.S. Pat. No. 3,791,960, in which $H_2$/HC is respectively between 0.2 and 10 and between 0.1 and 15, as well as U.S. Pat. No. 4,113,789 and U.S. Pat. No. 4,149,993, in which $H_2$/HC is approximately 0.2.

More recently, U.S. Pat. No. 4,804,803 claims the use of a monometallic catalyst having a greater resistance to deactivation, more particularly in the presence of sulphur, in a process for the isomerization of normal paraffins and without hydrogen recycling, using $H_2$/HC molar ratios in the effluent of below 0.05. These low ratios minimize the costs of the process, because they require no hydrogen separation apparatus or compressor for the recycling thereof.

SUMMARY OF THE INVENTION

The object of the present invention is the use of a novel bimetallic catalyst (incorporating at least two metals) based on chlorinated alumina and having, apart from a high selectivity and activity, a considerably improved coking resistance and therefore stability, permitting the use thereof in a process for the isomerization of normal $C_4$-$C_6$ paraffins not requiring hydrogen recycling and with a longer cycle time.

The catalyst according to the invention is based on chlorinated eta alumina containing 0.01 to 0.4 and preferably 0.015 to 0.025% by weight of a metal from group IV A of the periodic classification of elements, such as tin or germanium and preferably tin, 0.05 to 0.6 and preferably 0.15 to 0.4% by weight of a metal of group VIII of the periodic classification of elements, preferably platinum, and 1 to 12 and preferably 4 to 10% by weight of chlorine.

The preferred alumina is eta alumina, which leads to a regeneratable catalyst particularly due to its greater chlorination facility associated with its high specific surface of approximately 400 $m^2$/g (R. G. MCCLUNG, J. S. SOPKO et al, 1990, NPRA, Annual Meeting San Antonio).

The catalyst according to the invention can be prepared by different alumina impregnation methods, but the invention is not limited to a particular method. The impregnation operation, e.g., consists of contacting the alumina and an aqueous or organic solution of a compound of the chosen metal or metals, the volume of said solution being in excess or equal to the alumina retention volume.

The metal of group VIII, preferably platinum, is thus generally deposited on the alumina by anion exchange with a hexachloroplatinic acid solution. It is also possible to use other compounds of said acid, such as ammonium chloroplatinate, bromoplatinic acid or platinum chloride.

The metal of group IV A, generally tin or germanium, can be deposited on the alumina already preimpregnated by the metal of group VIII and optionally calcined and/or reduced, in an aqueous or hydrocarbon solution. This metal can be introduced by means of compounds such as chlorides, nitrates, sulphates, acetates, amino complexes of tin or germanium in aqueous solution and germanium or tin metallic aryl or alkyl compounds such as tetrabutyl tin, tetremethyl tin, diphenyl tin, tetrapropyl germanium and diphenyl germanium in hydrocarbon solution.

Once the metals are fixed to the alumina, the catalyst advantageously undergoes an activation treatment under hydrogen and at elevated temperature, e.g., at between approximately 300° and 500° C., in order to obtain an active metal phase. The procedure of this treatment under hydrogen e.g., consists of slowly raising the temperature under a hydrogen flow to the maximum reduction temperature, which is generally between approximately 300° and 500° C. and is preferably between approximately 340° and 470° C., followed by the maintaining of said temperature for 1 to 6 hours and preferably 1.5 to 4.5 hours.

The chlorination of the alumina takes place outside or directly in the isomerization unit using any known chlorinating agent, such as e.g. carbon tetrachloride, dichloroethane or dichloropropane, e.g. at a temperature between approximately 200° and 350° C.

The catalyst according to the invention is advantageously used in a process for isomerizing a charge rich in normal $C_4$-$C_6$ paraffins without hydrogen recycling, which constitutes another object of the invention.

The term "rich" means that the charge contains at least 50% and preferably at least 80% normal $C_4$-$C_6$ paraffins. The preferred charges are essentially constituted by normal $C_4$–$C_6$ paraffins. These charges are, e.g., n-butane and/or $C_5$–$C_6$ fractions, e.g., resulting from direct distillation or catalytic reforming.

The charge is advantageously carefully dried and preferably contains less than 0.2 ppm water and less than 0.5 ppm sulphur and nitrogen, due to the sensitivity to water and impurities of platinum catalysts based on chlorinated alumina. In order to achieve such contents, it is possible to use known, specific adsorbents.

In the isomerization process according to the invention a mixture constituted by the charge and hydrogen is contacted in a reaction zone with at least one catalyst according to the invention and described hereinbefore under isomerization conditions.

The isomerization conditions in the reaction zone and in particular the temperature are dependent on the charge to be treated. As isoparaffins are favored at low temperatures, from a thermodynamic standpoint, the performance characteristics of the catalyst will improve when working at lower temperatures. The temperature in the reaction zone is normally between 40° and 230° C. In cases where the charge essentially contains n-butane or essentially normal $C_4$–$C_6$ paraffins, the temperature is normally between 130° and 230° C. and preferably between 140° and 220° C. In the case where the charge essentially contains normal $C_5$–$C_6$ paraffins, the isomerization is easier to carry out and the temperature is then usually between 40° and 190° C. and preferably between 70° and 170° C. The pressure in the reaction zone can vary within a relatively wide range and is normally between 10 and 50 bars, preferably between 15 and 35 bars. The charge flow rate in the reaction zone can also vary within a relatively wide range, the space velocity normally being between 0.4 and 15 $h^{-1}$, preferably between 1 and 5 $h^{-1}$.

A chlorine concentration in the reaction zone is maintained at between 20 and 1000 ppm, preferably between 50 and 300 ppm. Thus, in order to maintain the chlorine content of the catalyst and therefore its acidity, it is necessary to continuously inject into the reaction zone, e.g., by means of the charge, a chlorine promoter, such as carbon tetrachloride or hydrogen chloride.

The hydrogen quantity mixed with the charge is such that the effluent drawn off from the reaction zone has a molar hydrogen/hydrocarbon ($H_2/HC$) ratio below 0.05.

The molar hydrogen/hydrocarbon ($H_2/HC$) ratio of the charge is then very low and generally below 0.1, which is made possible by the improved coking resistance of the catalyst used.

The effluent from the reaction zone is separated into a mixture of $C_4$–$C_6$ hydrocarbons incorporating the $C_4$–$C_6$ isoparaffins obtained and possibly normal $C_4$–$C_6$ paraffins not yet converted and a gaseous mixture containing hydrogen and light hydrocarbons, said gaseous mixture being eliminated from the process without hydrogen recycling. The cost of the process is very low, because it does not require a hydrogen separating apparatus or a compressor for the recycling thereof. The unconverted normal $C_4$–$C_6$ paraffins contained in the effluent from the reaction zone are generally recycled, at least in part, to the said reaction zone.

The reaction zone can optionally have at least two reactors in series in which the temperatures are different, the temperature in the second reactor generally being below that in the first reactor.

The following examples illustrate the invention without limiting the scope.

The catalytic performance characteristics are expressed by the ratios $$\frac{iC_x}{(i+n)C_x},$$

in which x is 4, 5 or 6, $iC_x$ representing the isoparaffin quantity with x carbon atoms in the effluent and $(i+n)C_x$ represents the isoparaffin and normal paraffin quantity with x carbon atoms in the effluent and the approaches to equilibrium on the different isomers defined hereinafter:

$$AEQi_x = \frac{\left(\frac{iC_x}{(i+n)C_x}\right) \text{in the effluent}}{\left(\frac{iC_x}{(i+n)C_x}\right) \text{at equilibrium}}$$

with $i_x$=isoparaffin with x carbon atoms (x=4, 5 or 6).

EXAMPLE 1: CATALYST A (ACCORDING TO THE INVENTION)

Following the prior calcination of the eta alumina, deposition takes place thereon of 0.3% platinum by anion exchange with hexachloroplatinic acid in the presence of HCl as the competing agent. The thus prepared solid is calcined and then reduced at 350° C. 200 ppm of tin are then deposited, while refluxing for 5 hours under an inert gas in a heptane solution containing tetrabutyl tin the previously prepared solid. The solution is then eliminated and replaced by a fresh heptane solution. The solid is washed for 2 hours under reflux in said solution. The solution is then eliminated and the solid is dried in a rotary evaporator. The thus prepared solid is fed into a reactor and then directly reduced within the latter at 450° C. for 4 hours. This is followed by chlorination at 280° C. by the injection of $CCl_4$ at a rate of 0.3 cm$^3$ of $CCl_4$ per gram of catalyst. The chlorine content on the final catalyst is then approximately 6% by weight.

EXAMPLE 2: CATALYST B (NOT ACCORDING TO THE INVENTION)

Catalyst B differs from catalyst A prepared in example 1 solely in that it does not contain tin. The platinum deposition, heat treatment and chlorination stages are identical to those described in example 1.

EXAMPLE 3: ISOMERIZATION TEST FOR NORMAL C—C PARAFFINS

The previously prepared catalysts A and B are each tested in the isomerization of a charge formed from approximately 60% normal $C_5$ paraffins and 40% normal $C_6$ paraffins, said charge containing 100 ppm of $CCl_4$, expressed as chlorine weight, for maintaining the chlorine content of the catalyst used.

The operating conditions are as follows:
Temperature: 150° C.
Pressure: 20 bars
Space velocity: 2 $h^{-1}$
$H_2/HC$ (in the effluent): 0.05.

The performance characteristics after 24 and 2160 hours of operation are given in table 1, there being essentially no deactivation of catalyst A, but a significant deactivation of catalyst B.

EXAMPLE 4: ISOMERIZATION TEST FOR N-BUTANE

Previously prepared catalysts A and B are each tested in the isomerization of a n-butane charge containing 100 ppm of $CCl_4$, expressed as chlorine weight.

The operating conditions are as follows:
Temperature: 200° C.
Pressure: 20 bars
Space velocity: 2 $h^{-1}$
$H_2/HC$ (in the effluent): 0.05.

The performance characteristics obtained after 24 and 2160 hours of operation are given in table 2, there being no deactivation of catalyst A, but a significant deactivation of catalyst B.

EXAMPLE 4

The previously prepared catalyst B is tested under the same conditions as those of example 3, except that the $H_2/HC$ ratio (in the effluent) is higher, being namely 1.

The performance characteristics obtained after 24 and 2160 hours of operation are given in table 3, there being no deactivation of catalyst B.

TABLE 1

| | Catalysts | | | |
|---|---|---|---|---|
| | A | | B | |
| | After 24 h. | After 2160 h. | After 24 h. | After 2160 h. |
| $iC_5/(i + n)C_5$ | 0.762 | 0.760 | 0.762 | 0.70 |
| $iC_6/(i + n)C_6$ | 0.895 | 0.890 | 0.895 | 0.78 |
| AEQ $i_5$ (%) | 95.3 | 95.0 | 95.3 | 87.5 |
| AEQ 22 $DMC_4$ (%) | 87.8 | 87.0 | 87.8 | 75.6 |
| Cracking (% by weight) (secondary reaction) | 3.05 | 2.0 | 3.2 | 2.5 | with 22 $DMC_4$ = 2,2-dimethyl butane)

TABLE 2

| | Catalysts | | | |
|---|---|---|---|---|
| | A | | B | |
| | After 24 h. | After 2160 h. | After 24 h. | After 2160 h. |
| $iC_4 (i + n)C_4$ | 0.5 | 0.5 | 0.5 | 0.4 |
| $AEQi_4$ (%) | 100 | 100 | 100 | 80 |
| Cracking (% by weight (secondary reaction) | 2.2 | 2.0 | 2.5 | 2.2 |

TABLE 3

| | Catalyst B | |
|---|---|---|
| | After 24 h. | After 2160 h. |
| $iC_5/(i + n)C_5$ | 0.762 | 0.760 |
| $iC_6/(i + n)C_6$ | 0.895 | 0.890 |
| $AEQi_5$ (%) | 95.3 | 95.0 |
| AEQ 22 $DMC_4$ (%) | 87.8 | 87.0 |
| Cracking (% by weight) (secondary reaction) | 3.2 | 3.0 |

We claim:

1. A catalyst composition consisting essentially of eta alumina; 0.01% to 0.4% by weight of a group IV A metal wherein said group IV A metal is germanium or tin; 0.05% to 0.6% by weight of platinum; and 1% to 12% by weight of chlorine.

2. A catalyst according to claim 1, wherein the weight content of germanium or tin is 0.015%–0.25%, the weight content of platinum is 0.15%–0.4% and the weight content of chlorine is 4%–10%.

3. A catalyst composition according to claim 1 wherein said metal of group IV A is germanium.

4. A catalyst composition according to claim 1 wherein said metal of group IV A is tin.

5. A process for the isomerization of a charge rich in normal $C_4$–$C_6$-paraffins without hydrogen recycling, comprising:
   contacting a mixture of said charge and hydrogen in a reaction zone with at least one catalyst according to claim 1 under isomerization conditions;
   maintaining a chlorine concentration in said reaction zone at 20 ppm–1000 ppm; and
   separating effluent from said reaction zone into $C_4$–$C_6$-isoparaffins and a gaseous mixture containing hydrogen, said gaseous mixture being eliminated from said process without recycling the hydrogen to said reaction zone,
   wherein the hydrogen quantity mixed with said charge is such that the effluent from said reaction zone has a hydrogen/hydrocarbon molar ratio of below 0.05.

6. A process according to claim 5, wherein said hydrogen/hydrocarbon molar ratio of the charge is below 0.1.

7. A process according to claim 5, wherein in said reaction zone, the temperature is 40° C.–230° C., the pressure is 10 bars–50 bars and the space velocity is 0.4 $h^{-1}$–15 $h^{-1}$.

8. A process according to claim 5 wherein the unconverted normal $C_4$–$C_6$ paraffins contained in said effluent from said reaction zone are at least partly recycled to said reaction zone.

9. A process according to claim 5 wherein said reaction zone has at least two reactors in series.

10. A catalyst composition according to claim 2, wherein said metal of group IV A is germanium.

11. A catalyst composition according to claim 2, wherein said metal of group IV A is tin.

12. A catalyst composition according to claim 11, produced by a process comprising:
   (a) calcining eta alumina,
   (b) depositing platinum on said eta alumina by anion exchange with hexachloroplatinic acid in the presence of HCl,
   (c) calcining the resultant composition and reducing the resultant calcined composition,
   (d) refluxing the resultant reduced composition in a solution containing a tin compound and drying the resultant tin-impregnated composition,
   (e) reducing the resultant dried catalyst composition, and
   (f) chlorinating the resultant reduced composition from the prior step.

13. A catalyst composition according to claim 12, wherein the resultant calcined composition is reduced at 350° C. in step (c) and the dried catalyst is reduced at 450° C. in step (e) and is then chlorinated at 280° C. by the injection of carbon tetrachloride in step (f).

14. A catalyst composition according to claim 1, wherein the chlorine weight content of said catalyst is 4%–10%.

15. A catalyst composition consisting of eta alumina; 0.01%–0.4% by weight of germanium or tin; 0.05%–0.6% by weight of platinum; and 1%–12% by weight chlorine.

16. A catalyst composition according to claim 15, wherein the chlorine weight content of said catalyst is 4%-10%.

17. A catalyst composition according to claim 4, produced by a process comprising:
(a) calcining eta alumina,
(b) depositing platinum on said eta alumina by anion exchange with hexachloroplatinic acid in the presence of HCl,
(c) calcining the resultant composition and reducing the resultant calcined composition,
(d) refluxing the resultant reduced composition in a solution containing a germanium compound and drying the resultant germanium-impregnated composition,
(e) reducing the resultant dried catalyst composition, and
(f) chlorinating the resultant reduced composition from the prior step.

18. A catalyst composition according to claim 17, wherein said germanium compound is a chloride, nitrate, sulfate, acetate, amino complex, alkyl or aryl compound.

19. A catalyst composition according to claim 12, wherein said tin compound is a chloride, nitrate, sulfate, acetate, amino complex, alkyl or aryl compound.

20. A catalyst composition according to claim 19, wherein said tin compound is tetrabutyl tin, tetramethyl tin or diphenyl tin.

21. A catalyst composition according to claim 20, wherein said tin compound is tetrabutyl tin.

22. A catalyst composition according to claim 18, wherein said germanium compound is tetrapropyl germanium or diphenyl germanium.

23. A catalyst composition comprising eta alumina; 0.01% to 0.4% by weight of germanium or tin; 0.05% to 0.6% by weight of a single metal of group VIII of the periodic classification of elements wherein said metal is platinum; and 1% to 12% by weight of chlorine.

* * * * *